United States Patent
Quick et al.

[19]

[11] Patent Number: 5,857,999
[45] Date of Patent: Jan. 12, 1999

[54] SMALL DIAMETER INTRODUCER FOR LAPAROSCOPIC INSTRUMENTS

[75] Inventors: Richard L. Quick, Trabuco Canyon; John P. Greelis, Aliso Viejo, both of Calif.

[73] Assignee: Imagyn Medical Technologies, Inc., Newport Beach, Calif.

[21] Appl. No.: 435,646

[22] Filed: May 5, 1995

[51] Int. Cl.⁶ .................................................. A61M 29/00
[52] U.S. Cl. ........................ 604/107; 604/104; 604/164; 604/174; 604/264
[58] Field of Search ................................ 604/25, 42, 49, 604/51, 52–54, 96, 99, 104, 105, 106, 107, 164, 165, 167, 158, 169–171, 174, 175, 177, 178, 184, 185, 198, 264, 272, 273, 274, 283, 278, 117, 118–121; 128/4, 26, 751–754; 606/191, 192, 185, 198

[56] References Cited

U.S. PATENT DOCUMENTS

| | | |
|---|---|---|
| 1,621,159 | 3/1927 | Evans . |
| 2,556,783 | 6/1951 | Wallace . |
| 2,649,092 | 8/1953 | Wallace . |
| 3,039,468 | 6/1962 | Price . |
| 3,241,554 | 3/1966 | Coanda . |
| 3,253,594 | 5/1966 | Matthews et al. . |
| 3,261,357 | 7/1966 | Roberts et al. . |
| 3,344,791 | 10/1967 | Foderick . |
| 3,545,443 | 12/1970 | Ansari . |
| 3,713,447 | 1/1973 | Adair . |
| 3,799,172 | 3/1974 | Szpur . |
| 3,817,251 | 6/1974 | Hasson . |
| 3,993,079 | 11/1976 | De Gatztañondo . |
| 4,069,826 | 1/1978 | Sessions et al. . |
| 4,112,932 | 9/1978 | Chiulli . |
| 4,228,802 | 10/1980 | Trott . |
| 4,240,411 | 12/1980 | Hosono . |
| 4,393,873 | 7/1983 | Nawash et al. . |
| 4,571,241 | 2/1986 | Chistopher . |
| 4,601,710 | 7/1986 | Moll . |
| 4,608,965 | 9/1986 | Anspach, Jr. et al. . |
| 4,627,838 | 12/1986 | Cross et al. . |
| 4,654,030 | 3/1987 | Moll et al. . |
| 4,655,752 | 4/1987 | Honkanen et al. . |
| 4,861,334 | 8/1989 | Nawaz . |
| 4,869,717 | 9/1989 | Adair ........................................ 604/51 |
| 4,931,042 | 6/1990 | Holmes et al. . |
| 4,986,810 | 1/1991 | Semrad . |
| 4,995,868 | 2/1991 | Brazier . |
| 5,002,557 | 3/1991 | Hasson . |
| 5,073,166 | 12/1991 | Parks et al. . |
| 5,122,122 | 6/1992 | Allgood ................................... 604/174 |
| 5,147,316 | 9/1992 | Castillenti . |
| 5,176,697 | 1/1993 | Hasson et al. . |
| 5,203,773 | 4/1993 | Green . |
| 5,226,426 | 7/1993 | Yoon . |
| 5,238,218 | 8/1993 | Mackal ....................................... 251/10 |
| 5,290,249 | 3/1994 | Foster et al. . |
| 5,306,239 | 4/1994 | Gurmarnik et al. ...................... 604/51 |
| 5,454,365 | 10/1995 | Bonutti .................................. 600/204 |
| 5,454,790 | 10/1995 | Dubrul ................................... 604/104 |
| 5,549,595 | 8/1996 | Freitas ........................................ 606/1 |
| 5,637,097 | 6/1997 | Yoon ....................................... 604/174 |

*Primary Examiner*—Wynn Wood Coggins
*Assistant Examiner*—Cris L. Rodriguez
*Attorney, Agent, or Firm*—Burns, Doane, Swecker & Mathis, L.L.P.

[57] ABSTRACT

An introducer is shown and described which includes a number of unique and useful features designed to improve the process of obtaining access to a bodily cavity for the purpose of performing minimally invasive surgical procedures, particularly laparoscopic procedures. These features include, among others, a sharpened cannula distal end, in order to assist entry of the introducer through the tissue barrier into the bodily cavity, a substantially transparent support disk so that visual access to the insertion site is maintained at all times, a septum seal designed to sealingly receive instruments having a cross-sectional dimension of 2.2 mm or less, an improved anchoring device which is simply and manually actuated and is of an advantageous three-slit design, and a simple, side-mounted gas insufflation port, usable at all times during the procedure and adapted for connection to gas tubing fitted with a pinch clamp for easy control of the gas flow.

11 Claims, 3 Drawing Sheets

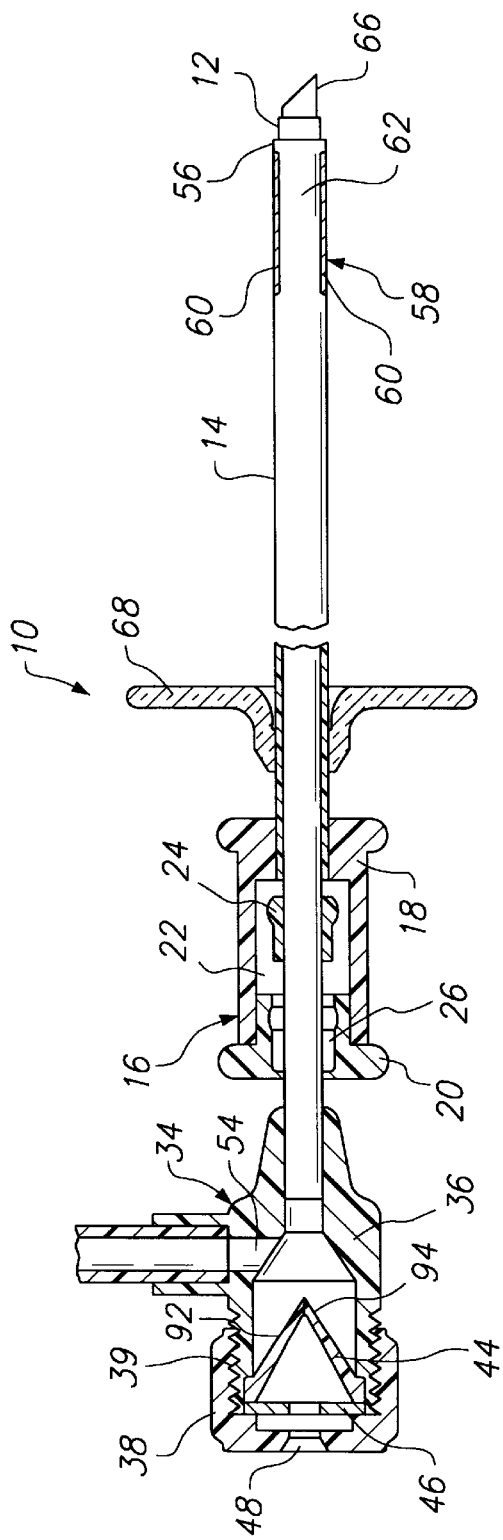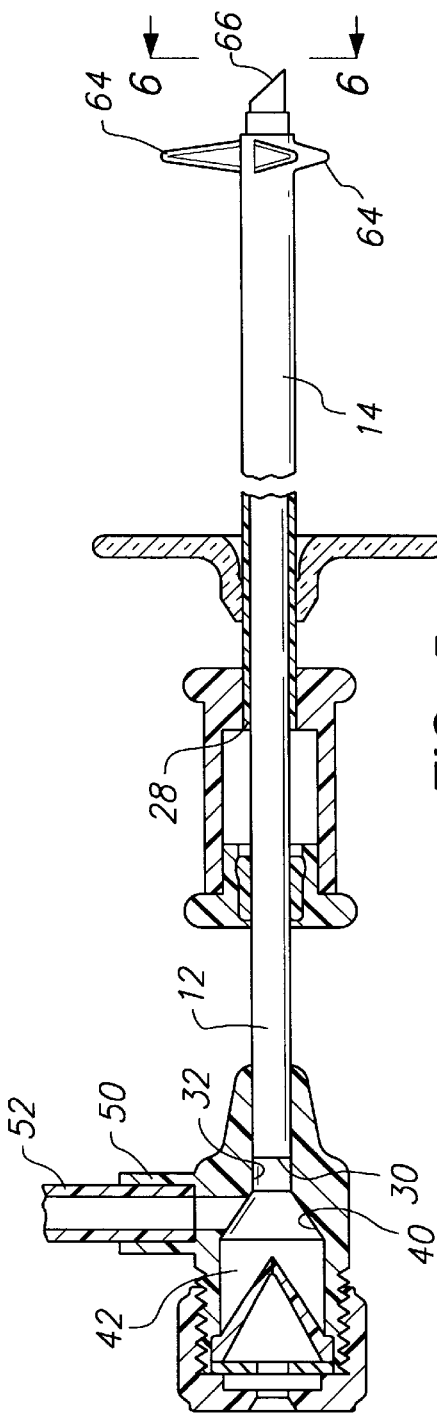

SMALL DIAMETER INTRODUCER FOR
LAPAROSCOPIC INSTRUMENTS

BACKGROUND OF THE INVENTION

This invention relates generally to surgical access introducers, and more particularly to access introducers for performing minimally invasive surgical procedures such as endoscopic and laparoscopic procedures.

Trocars or introducers having a cannula for use as a conduit for endoscopic or laparoscopic instruments in the performance of surgical procedures within bodily cavities such as the abdomen are well known in the art. However, the prior art devices heretofore available have a number of deficiencies. First, known devices are adapted to be used with 5 mm, 10 mm, or 12 mm instruments, but none to date have been adapted for instruments as small as 2.2 mm or less in cross-section. Furthermore, most prior art devices typically have complex, semi or fully automatic anchoring devices for retaining the introducer in position within the bodily cavity. These devices may comprise inflatable balloons or mushroom hinges, and typically employ spring biased mechanisms which react to either a manual or automatic triggering stimulus to deploy the anchoring device. Such devices are complex and expensive to manufacture.

An additional problem inherent in prior art introducer devices which employ associated anchoring mechanisms is that the cannula requires a thicker wall structure in order to support the anchoring mechanism and associated forces which are generated through the anchoring process. These thicker wall structures result in the requirement of additional forces on the part of the physician to insert the introducer. Introducer devices are typically inserted into the desired bodily cavity using an entry device, such as a Veress needle or other type of puncturing implement, which has a sharp needle for insertion into the tissue barrier surrounding the bodily cavity. The Veress needle is placed through the lumen of the introducer device so that its needle end extends distally past the distal end of the introducer in order to initiate the insertion procedure. However, since the needle end of the Veress needle is substantially narrower than the cross-sectional area of the introducer, particularly with the thickened cannula walls necessary to support the anchoring device, a substantial insertion force is required to insert the introducer device through the incision created by the Veress needle, and tearing of the tissue surrounding the insertion site often occurs.

Yet another problem encountered in prior art introducer devices concerns the routine implementation of a relatively large support disk, which is designed to slide axially along the exterior surface of the introducer cannula after insertion into the bodily cavity, until it rests against the outside surface of the tissue barrier, at the insertion site, in order to provide support for the introducer and associated surgical instruments during the ensuing surgical procedure and to prevent inadvertent extension of the access cannula into the bodily cavity. Unfortunately, it is often desirable to visually access the insertion site during the surgical procedure, in order to ascertain whether the site is torn or bleeding, or whether there is excessive leakage of fluids from the bodily cavity, and the support disk obscures this visual access.

SUMMARY OF INVENTION

The foregoing and other problems are solved by the inventive introducer shown and described herein, which includes a number of unique and useful features designed to improve the process of obtaining access to a bodily cavity for the purpose of performing minimally invasive surgical procedures. These features include, among others, a sharpened cannula distal end, in order to assist entry of the introducer through the tissue barrier into the bodily cavity, a substantially transparent support disk so that visual access to the insertion site is maintained at all times, a septum seal designed to sealingly receive instruments having a cross-sectional dimension of 2.2 mm or less, an improved anchoring device which is simply and manually actuated and is of an advantageous three-slit design, and a simple, side-mounted gas insufflation port, usable at all times during the procedure and adapted for connection to gas tubing fitted with a pinch clamp for easy control of the gas flow.

More particularly, an introducer or trocar for use as a conduit for endoscopic instruments and endoscopes in surgical procedures within a bodily cavity is provided, which comprises an inner cannula defining a lumen and an outer sheath coaxially surrounding the inner cannula. A distal end portion of the outer sheath is fixedly attached to a portion of the outer cannula, while the remaining portion of the outer sheath is adapted to be axially slidable relative to the cannula. Advantageously, the cannula includes a distal end portion comprising a sharp cutting surface for assisting the entry of the introducer into the bodily cavity. A distal portion of the sheath includes an anchoring device which comprises a plurality of slits, preferably three, arranged proximally of the fixedly attached portion. Thus, when the sheath is slid distally with respect to the cannula, strips of sheath material between each of the slits are expanded to form deployed wings for anchoring the introducer.

Attached to a proximal end of the sheath is a sliding handle, which is adapted to assist in sliding the sheath relative to the cannula in order to deploy and retract the anchoring device. The sliding handle includes a stop mechanism to prevent inadvertent overexpansion of the wings, by preventing excessive distal sliding movement of the sheath relative to the cannula.

Another advantageous feature of the invention is the provision of an insufflation gas entry port which is mounted on a side portion of the introducer and is adapted to deliver insufflation gas to the bodily cavity through the lumen at any time when the introducer is inserted into the bodily cavity. Gas tubing is attached to the gas entry port for supplying the gas, and a pinch clamp is disposed about the tubing and adapted to pinch the tubing shut when it is desired to prevent the flow of insufflation gas into the introducer.

A substantially fluid-tight septum seal is provided in a proximal portion of the introducer, and is adapted to maintain a fluid-tight sealing relationship about an instrument having a cross-sectional dimension of 2.2 mm or less, unlike prior art devices, which are considerably larger.

In another aspect of the invention, an introducer is provided for use as a conduit for endoscopic instruments and endoscopes in surgical procedures within a bodily cavity, which comprises an inner cannula defining a lumen and an outer sheath coaxially surrounding the inner cannula. The outer sheath includes a distal end portion which is fixedly attached to a portion of the cannula, while the remaining portion of the outer sheath is adapted to be axially slidable relative to the cannula. An exterior support disk is mounted on and adapted to be slid along the outer sheath when the introducer is inserted through a tissue barrier into the bodily cavity, such that it rests against the exterior surface of the tissue barrier. Advantageously, the support disk is sufficiently transparent to permit visual access to the tissue barrier insertion site.

In still another aspect of the invention, a method of operating an introducer for use as a conduit for endoscopic instruments and endoscopes in surgical procedures within a bodily cavity is disclosed, wherein the introducer includes an inner cannula defining a lumen and an outer sheath coaxially surrounding the inner cannula. The method comprises inserting an entry instrument, such as a Veress needle, having a sharp distal end into the introducer, such that it extends through the lumen with the sharp distal end thereof protruding from the distal end of the cannula. The introducer is advanced through a tissue barrier defining the bodily cavity until a distal portion thereof is fully inserted into the cavity. Then, the bodily cavity is insufflated by introducing gas into the lumen through a side port on the introducer. The flow of insufflation gas is stopped once a predetermined insufflation gas pressure is attained. A surgical instrument may be inserted into the introducer cannula at any time during the procedure, such that it extends through the lumen and protrudes into the bodily cavity from the distal end of the cannula. When necessary, because the insufflation pressure has fallen below a predetermined level, the bodily cavity is re-insufflated by re-introducing gas through the side port.

In yet another aspect of the invention, a method of operating an introducer for use as a conduit for endoscopic instruments and endoscopes in surgical procedures within a bodily cavity is disclosed, wherein the introducer includes an inner cannula defining a lumen and an outer sheath coaxially surrounding the inner cannula. The method comprises inserting an entry instrument, such as a Veress needle, having a sharp distal end into the introducer, such that it extends through the lumen with the sharp distal end thereof protruding from the distal end of the cannula. The introducer is advanced through a tissue barrier defining the bodily cavity until a distal portion thereof is fully inserted into the cavity. Then, a surgical instrument is inserted into the introducer cannula, such that it extends through the lumen and protrudes into the bodily cavity from the distal end of the cannula. A substantially transparent exterior support disk is slid along the sheath until it rests against an exterior surface of the tissue barrier at the introducer insertion site. Once in place, the insertion site may be viewed through the exterior support disk, when desired.

The invention, together with additional features and advantages thereof, may best be understood by reference to the following description taken in conjunction with the accompanying illustrative drawing.

BRIEF DESCRIPTION OF THE DRAWINGS

FIG. 4 is a cross-sectional view of the inventive introducer, illustrating the introducer with the expanding wings in their retracted position;

FIG. 5 is a cross-sectional view similar to FIG. 4, illustrating the expanding wings in their deployed position.

DETAILED DESCRIPTION OF THE DRAWINGS

Figure 6:
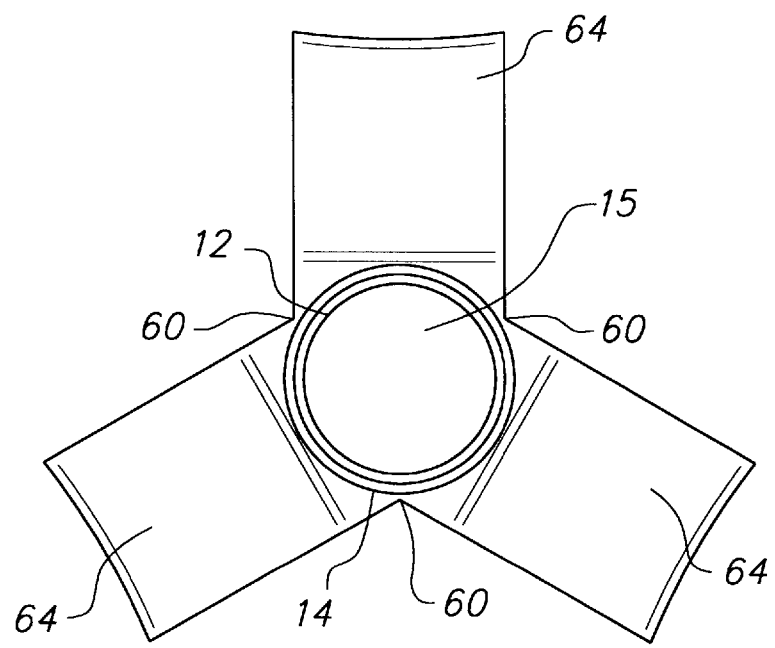
FIG. 6 is an end view of the inventive introducer, taken along lines 6—6 of FIG. 5.

Referring now to FIGS. 4, 5, and 6, a preferred embodiment is shown of an introducer or trocar 10 according to the invention. The introducer 10 includes an inner cannula 12 and a cylindrical outer sheath 14. The inner cannula 12 is preferably fabricated of a biocompatible metal, such as stainless steel, and defines a lumen 15 (FIG. 6) which extends axially through the entire length of the cannula. In the preferred embodiment, the lumen has a cross-sectional area of approximately 2.3 mm, in order to accommodate surgical instruments having a cross-sectional dimension of 2.2 mm or less. The outer sheath 14 is preferably fabricated of a durable flexible material, such as plastic. To the proximal end of the outer sheath 14 is affixed a sliding handle 16. The sliding handle 16 comprises an outer cylindrical housing 18 and a handle portion 20, both of which are preferably fabricated of molded plastic. Enclosed within the sliding handle 16 is an inner cavity 22, a snap ring stop 24, and a snap ring receiving chamber 26. In the illustrated preferred embodiment, the snap ring stop 24 is fixedly mounted, preferably by means of adhesive, about the inner cannula 12. Alternatively, it could be made to be integral with the cannula As the sliding handle translates linearly in conjunction with translation of the outer sheath 14, as will be described in more detail below, the snap ring stop 24 is located either in the inner cavity 22 (FIG. 4) or in the snap ring receiving chamber 24 (FIG. 5). The proximal end 28 of the outer sheath 14 extends proximally into the distal end of the sliding handle 16, and is adhesively affixed thereto, terminating at the distal end of the inner cavity 22. Of course, if desired, alternative affixation techniques, other than adhesive, could be used to affix the outer sheath 14 to the sliding handle 16, and to affix the snap ring stop 24 to the inner cannula 12.

The proximal end 30 of the inner cannula 12 is received within and fixedly attached to the cylindrical wall of a passage 32 extending through a distal portion of a T-connector 34. The T-connector 34 is preferably made of molded plastic, like the sliding handle 16, and is of a two-piece construction, comprised of a housing portion 36 and a cap portion 38, which is threadedly attached to the housing portion 36 and preferably permanently adhered thereto at the threads 39 once threaded into place. Alternatively, rather than being threaded to the housing portion 36, the cap portion could be bayonetted or snapped into place, for example.

Proximally of the terminus of the proximal end 30 of the inner cannula 12, the passage 32 widens into a conical transition portion 40, which in turn widens into a valve chamber 42. Within the valve chamber 42 is disposed a duckbill valve 44, as well as a flexible washer seal 46, preferably of silicone or a similar material, which together are adapted to sealingly receive an instrument which enters through an access port 48 in the cap portion 38. An acceptable alternative to the duckbill valve 44 is a star valve, which has a plurality of star-type slits rather than the single slit of a conventional duckbill valve. The passage 32 and the cannula lumen 12 are fluidly connected to create a continuous axial passageway from the access port 48 to the distal end of the cannula 12.

Since the inventive introducer 10 is particularly adapted for laparoscopic surgical procedures, insufflation of the abdominal cavity is normally required. Therefore, the housing portion 36 of the T-connector 34 may further include a side-mounted gas entry port 50, as illustrated, to which is fluidly connected a gas tube 52. A gas passage 54 fluidly connects the gas tube 52 to the passage transition portion 40, from whence the insufflation gas may flow through the inner cannula 12 into the abdominal cavity. However, in the event that a plurality of introducers are to be used to accomplish a particular surgical procedure, the other introducers for the secondary access ports may omit the insufflation port feature, though, of course, a septum valve is still required to prevent leakage of pressurized gas from the bodily cavity.

At the distal end of the introducer 10, a distal portion 56 of the outer sheath 14 is fixedly attached to the inner cannula 12, again preferably using an adhesive, though other methods of permanent attachment may be used as well. The entire remaining portion of the outer sheath 14 is free to slide axially over the coaxial inner cannula 12, for a purpose which will be described. Proximally of the attached portion 56 is an expanding wing anchoring device 58, which is comprised of a plurality of slits 60 (preferably three—see FIG. 6) in the outer sheath 14. It is designed such that when the outer sheath 14 is slid distally with respect to the inner cannula 12, the fixed attached portion 56 causes the strips 62 between the slits 60 to expand outwardly, as illustrated in FIGS. 5 and 6, creating expanded wings 64. The strips 62 are each preferably creased to create a hinge about halfway along their length, in a transverse orientation, in order to ensure the proper and efficient expansion of the wings upon distal movement of the sheath 14. The expanding wing anchoring device 58 on the sheath 14 is preferably located just proximate to the distal end of the cannula, in order to minimize the cannula length within the bodily cavity. Applicants have found that three slits, which result in three corresponding expanding wings, produce decidedly superior results, maximizing the coverage area of the wing apparatus.

A significant feature of the invention is the provision of a sharpened cutting surface 66, which may be bevelled or conically configured, at the distal end of the inner cannula 12 (FIGS. 4 and 5). This cutting surface 66 is adapted to assist the entry of the introducer into the patients body.

Between the expanding wing anchoring device 58 and the sliding handle 16 is an exterior support disk 68, which is slidably disposed about the outer sheath 14. Its function is to stabilize the protruding portion of the introducer once placed into the body, and is maintained on the introducer by friction of the outer sheath 14 to the support disk. This support disk 68 is preferably comprised of resilient material (such as silicone or polyurethane), which is sufficiently transparent to permit visual access to the insertion site during the procedure.

Figure 1:
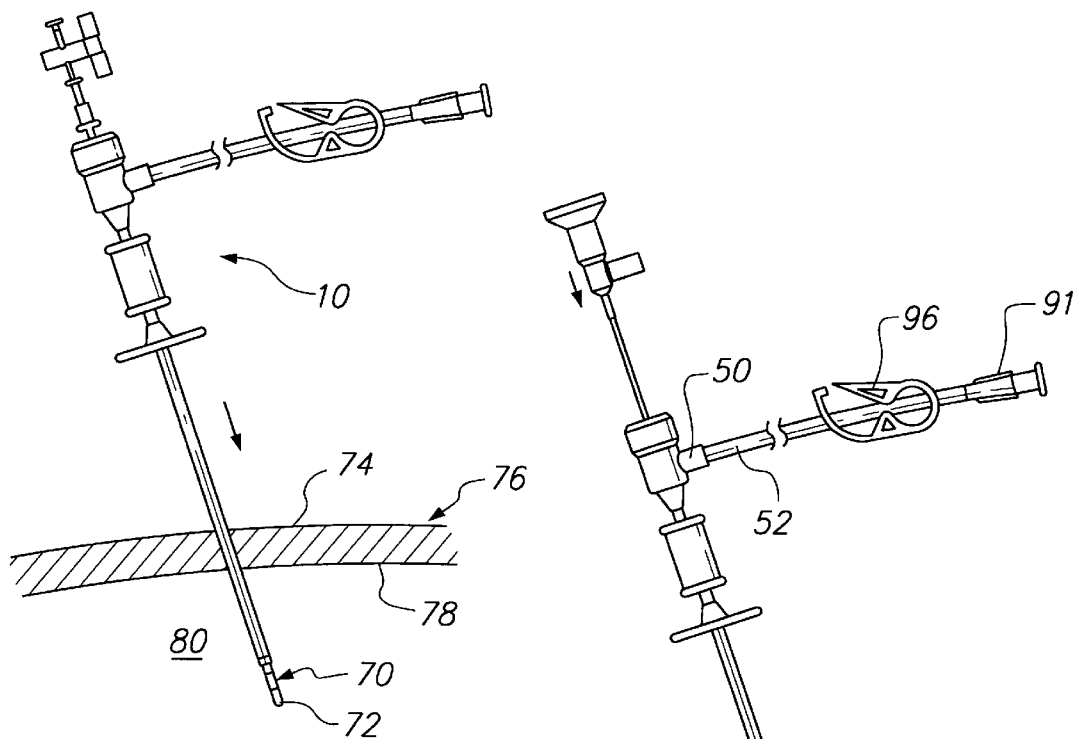
FIG. 1 illustrates an introducer or trocar according to the present invention, having a Veress needle inserted therethrough and in the process of entering the abdominal cavity of a patient.

Now referring more particularly to FIGS. 1, 1A, 2, and 3, a preferred method of operating and utilizing the inventive introducer 10 will be explained. Initially, the introducer 10 is placed into the body using a Veress needle 70, as illustrated in FIG. 1, though other entry instruments, such as puncturing implements or pneumoperitoneum needles, may be alternatively utilized. As is well known in the prior art, the Veress needle comprises a spring-loaded blunt inner member disposed within a hollow needle, wherein the blunt inner member is normally biased to extend distally beyond the terminus of the needle, in order to prevent inadvertent damage to internal organs. Procedurally, the Veress needle 70 is inserted into the introducer 10 through the access port 48 until its distal cutting end 72 slides completely through the cannula lumen 15, extending distally beyond the sharpened cutting surface 66 at the distal end of the cannula 12.

Then, in known fashion, the blunt inner member of the Veress needle is pressed against the exterior surface 74 of the abdominal wall 76, until the point of the hollow needle is exposed and penetrates the abdominal wall. Preferably using the thumb and forefingers, the Veress needle/introducer combination is advanced through the abdominal wall 76 until it pops through the interior surface 78 of the wall, entering the abdominal cavity 80 (FIG. 1). Immediately, as the pressure ceases against the blunt inner member of the Veress needle, it returns to its advanced position beyond the needle point, due to the biasing force of the spring, in order to protect internal organs and prevent further cutting.

Figure 1A:
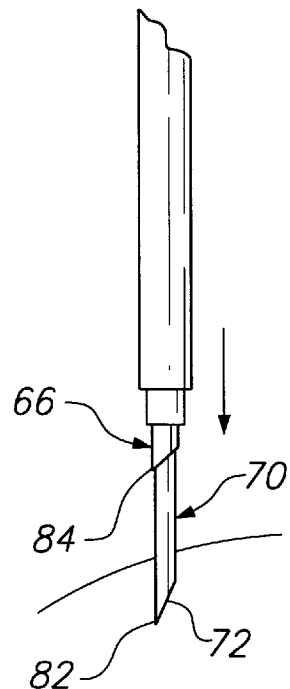
FIG. 1A illustrates the cutting edges of the Veress needle and introducer sheath shown in FIG. 1, as they enter through the abdominal wall of the patient.

As illustrated best in FIG. 1A, the distal cutting end 72 of the Veress needle is typically bevelled and conically shaped in a similar configuration to that of the cutting surface 66 of the sheath 14, and having a point 82. As the Veress needle/introducer combination is advanced through the abdominal wall 76, the point 82 of the Veress needle is positioned distally of the cutting surface 66 and its point 84, so that the Veress needle point 82 penetrates first, after which the sheath point 84 follows. Because the cross-sectional area of the sheath cutting surface 66 is greater than the cross-sectional area of the Veress needle cutting surface, the sheath cutting surface 66 cuts additional tissue, enabling accommodation of the larger sheath cross-section without inadvertently tearing the abdominal wall tissue. In this manner, the sharpened cutting surface of the sheath helps to reduce the required insertion forces and thereby assists in placing the introducer 10 into the body and transporting the body of the cannula through the layers of tissue which comprise the abdominal wall.

As illustrated in FIG. 1A, it is preferred that the cutting surface 66 of the sheath and the cutting surface of the Veress needle be substantially aligned, so that the respective points 82 and 84 are in substantially the same circumferential orientation. To assist this alignment, engaging pins and slots or other known mechanisms for assisting the alignment of two elements could be employed. However, alignment is not a requirement, and the invention will fully function with the two cutting surfaces in different orientations, if desired.

Once the introducer 10 is fully inserted into the abdominal cavity, the Veress needle may be removed from the introducer by withdrawing it proximally therefrom. Then, insufflation of the abdominal cavity is preferably performed, by introducing pressurized gas, typically carbon dioxide ($CO_2$). This insufflation gas is introduced through a Luer connector 91 into the gas tube 52 and side-mounted gas entry port 50, then flows through the gas passage 54 into the lumen 15 of the cannula 12. The pressurized gas is prevented from leaking from the passage 32 by the duckbill valve 44, the leaflets 92 and 94 (FIGS. 4 and 5) of which are closed tightly together to seal the passage when no instrument is inserted through the access port 48. When the desired insufflation pressure is reached, the procedure can readily be halted by pinching the tubing 52 closed using a pinch clamp 96. Then, when it is necessary to re-insufflate the abdomen, during the surgical procedure, because of incidental gas leakage and the absorption of $CO_2$ gas into the patient's body, the attendant need only release the pinch clamp 96 to start the flow of gas through the tube 52 and the lumen 15 into the abdominal cavity. Alternatively, rather than using a pinch clamp, the source of insufflation gas may be directly activated and de-activated, as necessary.

Figure 2:
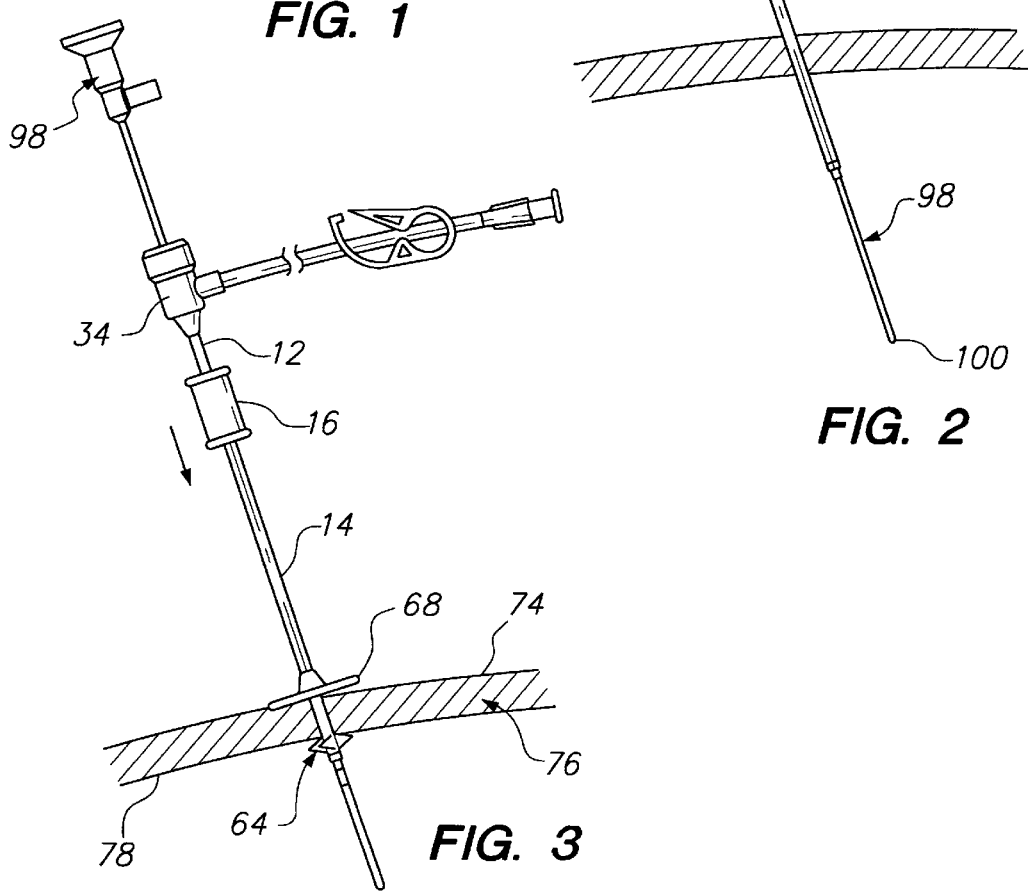
FIG. 2 illustrates the introducer of FIG. 1, after its entry into the abdominal cavity, wherein the Veress needle has been removed and an endoscope has been inserted in its place.
Figure 3:
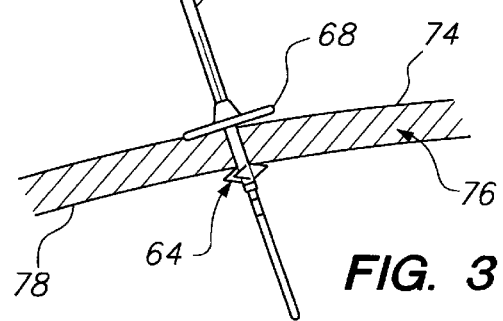
FIG. 3 illustrates the introducer of FIGS. 1 and 2, wherein the wings of the expanding wing anchoring device have been expanded to retain the introducer in position, and the exterior support disk has been slid to a position against the outer surface of the abdominal wall.

Once the abdominal cavity 80 has been fully insufflated, a surgical instrument 98, such as an endoscope or laparoscope, may be inserted into the introducer 10, in the same manner that the Veress needle 70 was previously inserted, such that the distal tip 100 of the instrument extends into the abdominal cavity beyond the distal end of the cannula 12 (FIG. 2). As the tip of the instrument enters through the access port 48, it passes through the flexible washer seal 46, and also through the leaflets 92 and 94 of the duckbill valve 44. The washer valve closes sealingly about the shaft of the instrument once it is inserted into the introducer, thereby sealing the access port 48 and preventing leakage of the insufflation gas and any other pressurized fluids contained in the abdominal cavity. Once fully inserted into the abdominal cavity, the introducer 10 is slid distally along the shaft of the instrument, until the exterior support disk or tissue clamp 68 rests against the outer surface 74 of the abdominal wall 76 (FIG. 3). Then, the expanding wing anchoring device is deployed by grasping the T-connector 34 with one hand and advancing the sliding handle 16 distally with the other hand. This causes the sheath 14 to slide axially in a distal direction with respect to the cannula 12. However, since the sheath 14 and cannula 12 are fixedly attached to one another at the distal attached portion 56, this relative sliding motion causes the strips 62 between the slits 60 (FIG. 4) to expand, so that the strips 62 become expanded wings 64. Once the wings 64 are fully deployed, the introducer body is withdrawn until the wings 64 anchor against the inner surface 78 of the abdominal wall.

In the preferred embodiment, the sliding handle 16 contains a mechanism which helps to prevent overexpansion of the wings 64. When the wings 64 are in their retracted position, as illustrated in FIG. 4, the snap ring stop 24 is located in the inner cavity 22. However, as the wings are deployed, and the sheath 14 moves distally with respect to the cannula 12, the sliding handle 16 also moves distally with respect to the fixed snap ring stop 24. Thus, after the sheath 14 has been slid distally a predetermined distance, the snap ring receiving chamber 26 engages the snap ring stop, as illustrated in FIG. 5, preventing further distal movement of the sheath 14 relative to the cannula 12. Because of this mechanism, the wings 64 cannot be expanded beyond a predetermined point, thereby preventing damage to the expanding wing anchoring device 58.

Once the wings 64 are fully deployed, and anchored against the inner surface 78 of the abdominal wall, the exterior support disk or tissue clamp 68 is slid distally along the sheath 14 until it is snugly positioned against the exterior surface 74 of the abdominal wall, to provide support for the introducer 10. At this juncture, the desired surgical procedure may be performed. Furthermore, because the disk 68 is transparent, the surgeon can view the insertion site through the disk if desired, in order to determine, for example, whether the site is torn or bleeding or if excess leakage from the abdominal cavity is occurring.

At the end of the procedure, the instrument 98 may be removed proximally from the introducer 10, following which the insufflation line 52 is disconnected. The pneumoperitoneum is permitted to escape through the sideport 50 by ensuring that the pinch clamp 96 is in the open position for a period of time after the conclusion of the procedure.

While this invention has been described with respect to various specific examples and embodiments, it is to be understood that the invention is not limited thereto and that it can be variously practiced within the scope of the following claims.

What is claimed is:

1. An introducer for use as a conduit for endoscopic instruments and endoscopes in surgical procedures within a bodily cavity, comprising:

an inner cannula defining a lumen;

an outer sheath coaxially surrounding said inner cannula, a distal end portion of said outer sheath being fixedly attached to a portion of said inner cannula, while the remaining portion of said outer sheath is adapted to be axially slidable relative to said inner cannula;

an anchoring device disposed on said outer sheath for anchoring the introducer to an inner surface of a tissue barrier defining said bodily cavity;

a sliding handle, said handle being adapted to assist in sliding said outer sheath relative to said inner cannula in order to deploy and retract said anchoring device;

said outer sheath being attached at a proximal end thereof to said sliding handle;

the inner cannula includes a distal end portion extending distally of the distal end portion of said outer sheath, the inner cannula distal end portion comprising a sharp cutting surface for assisting the entry of said introducer into said bodily cavity;

wherein said sliding handle includes a snap ring stop and a snap ring receiving chamber enclosed therein, said snap ring receiving chamber being adapted to engage said snap ring stop when said sliding handle is slid distally a predetermined distance, thereby preventing further distal movement of said outer sheath relative to said inner cannula.

2. An introducer for use as a conduit for endoscopic instruments and endoscopes in surgical procedures within a bodily cavity, and being adapted to be percutaneously introduced into said bodily cavity, the introducer comprising:

an inner cannula defining a lumen;

an outer sheath coaxially surrounding said inner cannula, a distal end portion of said outer sheath being fixedly attached to a portion of said inner cannula, while the remaining portion of said outer sheath is adapted to be axially slidable relative to said inner cannula;

the inner cannula including a distal end portion extending distally of the distal end portion of said outer sheath, the inner cannula distal end portion comprising a sharp cutting surface for assisting the entry of said introducer into said bodily cavity;

a needle disposed within said inner cannula lumen, the needle having a sharp distal end which extends distally of the distal end portion of the inner cannula for assisting the entry of said introducer into said bodily cavity;

said needle being adapted for removal after entry of the introducer into the bodily cavity, and the inner cannula being adapted to remain in said bodily cavity after removal of the needle, so that medical instruments may be inserted into said bodily cavity through said inner cannula lumen;

an anchoring device disposed on said outer sheath for anchoring the introducer to an inner surface of a tissue barrier defining said bodily cavity; and a sliding handle, wherein said outer sheath is attached at a proximal end thereof to said sliding handle, said sliding handle being adapted to assist in sliding said outer sheath relative to said inner cannula in order to deploy and retract said anchoring device in said sliding handle includes a snap ring stop and a snap ring receiving chamber enclosed therein, said snap ring receiving chamber being adapted to engage said snap ring stop when said sliding handle is slid distally a predetermined distance, thereby preventing further distal movement of said outer sheath relative to said inner cannula.

3. An introducer as recited in claim 2, wherein said anchoring device comprises a plurality of slits in a distal portion of said outer sheath, proximally of said fixedly attached portion, such that when said outer sheath is slid distally with respect to said inner cannula, strips of sheath material between each of said slits are expanded to form deployed wings for anchoring said introducer.

4. An introducer as recited in claim 2, where said plurality of slits comprises three slits.

5. An introducer as recited in claim 2, and further comprising a connector body, wherein said inner cannula is attached at a proximal end thereof to said connector body, said connector body comprising an instrument access port at a proximal end thereof, a septum seal for fluidly sealing said access port, and a passage extending therethrough.

6. An introducer as recited in claim 5, wherein said septum seal comprises a duckbill valve.

7. An introducer as recited in claim 5, and further comprising an insufflation gas port mounted on a side portion of said connector body.

8. An introducer as recited in claim 2, and further comprising an exterior support disk which is mounted on and adapted to be slid along said outer sheath when the introducer is inserted into said bodily cavity, such that it rests against the exterior surface of a tissue barrier defining said bodily cavity.

9. An introducer as recited in claim 8, wherein said support disk is sufficiently transparent to permit visual access to the site on the tissue barrier through which said introducer is inserted into the bodily cavity.

10. An introducer as recited in claim 2, wherein said lumen is adapted to receive instruments having a cross-sectional dimension of 2.2 mm or less.

11. An introducer as recited in claim 2, and further comprising a substantially fluid-tight septum seal in a proximal portion thereof, said septum seal being adapted to maintain a fluid-tight sealing relationship about an instrument having a cross-sectional dimension of 2.2 mm or less.

* * * * *